United States Patent
Osawa

(10) Patent No.: US 10,231,700 B2
(45) Date of Patent: Mar. 19, 2019

(54) ULTRASOUND PROBE AND CONNECTION METHOD FOR SIGNAL LINES

(71) Applicant: FUJIFILM Corporation, Tokyo (JP)

(72) Inventor: Atsushi Osawa, Ashigara-kami-gun (JP)

(73) Assignee: FUJIFULM Corporation, Tokyo (JP)

( * ) Notice: Subject to any disclaimer, the term of this patent is extended or adjusted under 35 U.S.C. 154(b) by 907 days.

(21) Appl. No.: 14/500,022

(22) Filed: Sep. 29, 2014

(65) Prior Publication Data

US 2015/0018687 A1 Jan. 15, 2015

Related U.S. Application Data

(63) Continuation of application No. PCT/JP2012/079248, filed on Nov. 12, 2012.

(30) Foreign Application Priority Data

Mar. 30, 2012 (JP) .................................. 2012-079989

(51) Int. Cl.
*A61B 8/00* (2006.01)
*A61B 8/14* (2006.01)
(Continued)

(52) U.S. Cl.
CPC .......... *A61B 8/4444* (2013.01); *A61B 8/4488* (2013.01); *B06B 1/0622* (2013.01);
(Continued)

(58) Field of Classification Search
CPC ............. H01L 41/0471; H01L 41/0475; A61B 8/4444; A61B 8/4488;
(Continued)

(56) References Cited

U.S. PATENT DOCUMENTS 3,651,432 A 3/1972 Henschen et al.
5,923,115 A * 7/1999 Mohr, III ............ H01L 41/0475
310/334

(Continued)

FOREIGN PATENT DOCUMENTS

| EP | 1 449 482 A1 | 8/2004 |
|---|---|---|
| EP | 2367405 A1 | 9/2011 |
| JP | 06-105396 A | 4/1994 |

OTHER PUBLICATIONS

Partial Supplementary European Search Report, dated Mar. 17, 2016, for European Application No. 12872531.4.

(Continued)

*Primary Examiner* — Thomas J Hong
*Assistant Examiner* — Helene C Bor
(74) *Attorney, Agent, or Firm* — Birch, Stewart, Kolasch & Birch, LLP

(57) ABSTRACT

An ultrasound probe includes a plurality of piezoelectric elements arranged in an array, a plurality of drawn-out signal lines drawn out from the plurality of piezoelectric elements, and a print board on which a plurality of connection conductors are formed for connecting between a plurality of communication cables connected to an ultrasound diagnostic apparatus body and the plurality of drawn-out signal lines, respectively, connection-conductor insulation layers being formed on the printed board so as to cover respective outer peripheries of the plurality of connection conductors, and a connection-conductor ground conductive layer being formed on the printed board so as to cover individual outer peripheries of the connection-conductor insulation layers, whereby the plurality of connection conductors are shielded from one another.

18 Claims, 3 Drawing Sheets

(51) Int. Cl.
*B06B 1/06* (2006.01)
*H01L 41/047* (2006.01)

(52) U.S. Cl.
CPC .............. *A61B 8/14* (2013.01); *A61B 8/4272* (2013.01); *H01L 41/0475* (2013.01)

(58) Field of Classification Search
CPC .......... B06B 1/06–1/0696; H03H 9/13–9/133; H01B 11/08; H01B 11/10; Y10S 439/941
USPC ........................ 310/334; 333/149, 24 R, 187
See application file for complete search history.

(56) References Cited

U.S. PATENT DOCUMENTS

| | | | | |
|---|---|---|---|---|
| 6,117,083 | A * | 9/2000 | Buck | H01B 7/041 600/459 |
| 6,798,059 | B1 * | 9/2004 | Ishihara | B06B 1/0622 257/700 |
| 8,410,666 | B2 * | 4/2013 | Shikata | B06B 1/064 29/594 |
| 8,624,469 | B2 * | 1/2014 | Dausch | B06B 1/0622 310/334 |
| 2001/0021807 | A1 * | 9/2001 | Saito | G10K 11/02 600/437 |
| 2005/0015010 | A1 | 1/2005 | Antich et al. | |
| 2006/0238067 | A1 * | 10/2006 | Dausch | A61B 8/4483 310/311 |
| 2007/0216257 | A1 * | 9/2007 | Fujimura | B06B 1/0651 310/326 |
| 2008/0114309 | A1 * | 5/2008 | Zuckerman | A61B 17/3403 604/264 |
| 2010/0241004 | A1 * | 9/2010 | Jung | B06B 1/0622 600/459 |
| 2013/0267853 | A1 * | 10/2013 | Dausch | B06B 1/0607 600/466 |

OTHER PUBLICATIONS

Extended European Search Report for European Application No. 12872531.4, dated Jun. 7, 2016.
International Preliminary Report on Patentability and English translation of the Written Opinion of the International Searching Authority (Forms PCT/IB/338, PCT/IB/373 and PCT/ISA/237), dated Oct. 9, 2014, for International Application No. PCT/JP2012/079248.
International Search Report, issued in PCT/JP2012/079248, dated Dec. 4, 2012.

* cited by examiner

ULTRASOUND PROBE AND CONNECTION METHOD FOR SIGNAL LINES

CROSS-REFERENCE TO RELATED APPLICATIONS

This application is a Continuation of PCT International Application No. PCT/JP2012/079248 filed on Nov. 12, 2012, which claims priority under 35 U.S.C. § 119(a) to Japanese Application No. 2012-079989 filed on Mar. 30, 2012. The above application is hereby expressly incorporated by reference, in its entirety, into the present application.

BACKGROUND OF THE INVENTION

The present invention relates to an ultrasound probe and a method for connecting signal lines, in particular, to an ultrasound probe having a plurality of signal lines which are drawn out from a plurality of piezoelectric elements and are connected to an ultrasound diagnostic apparatus body through communication cables and a method for connecting the signal lines.

Conventionally, ultrasound diagnostic apparatuses using ultrasound images have been put to practical use in the medical field. In general, an ultrasound diagnostic apparatus of this type transmits an ultrasonic beam from a plurality of piezoelectric elements of an ultrasound probe into a subject's body, receives the echo from the subject with the plurality of piezoelectric elements of the ultrasound probe, and electrically processes the resulting reception signals in an ultrasound diagnostic apparatus body to produce an ultrasound image.

Recently, in order to improve ultrasound image resolution, ultrasound probes that transmit and receive high-frequency ultrasonic beams have come into practical use. Through transmission and reception of high-frequency ultrasonic beams, ultrasonic echoes from objects that are present at short distances within a subject's body can be individually obtained, whereby the resolution can be improved. On the other hand, there has been a problem that use of a high-frequency ultrasonic beam in ultrasound diagnosis would easily invite noise mixture. For example, as signals have the higher frequency, reception signals respectively received by the plurality of piezoelectric elements of the ultrasound probe are likely to cause electric cross-talk among them. As a result, the signal-to-noise ratio of reception signals significantly drops. In addition, a high-frequency ultrasonic beam readily attenuates as propagating within the subject's body, which will be another cause of a decrease in the signal-to-noise ratio.

In order to suppress the decrease in the signal-to-noise ratio of reception signals, the plurality of reception signals received by the plurality of piezoelectric elements of the ultrasound probe are transmitted to the ultrasound diagnostic apparatus body through coaxial cables, respectively. In this manner, reception signals can be kept from being affected by electric cross-talk or the like, and the decrease in the signal-to-noise ratio of reception signals can be suppressed. On the other hand, it is difficult to thoroughly connect from the plurality of piezoelectric elements of the ultrasound probe to the ultrasound diagnostic apparatus body with coaxial cables. For example, drawn-out signal lines that are drawn out from signal electrodes of the plurality of piezoelectric elements to the outside are connected to the coaxial cables via connection conductors formed on a printed board. Since the drawn-out signal lines and the connection conductors are not shielded from each other, noises would be possibly mixed in reception signals transmitting therebetween.

Accordingly, as a technology for suppressing noise mixture into reception signals, there has been proposed provision of grounded conductive layers each being disposed between adjacent connection conductors formed on a printed board as disclosed, for example, in JP 06-105396 A.

In the ultrasound probe described in JP 06-105396 A, the respective grounded conductive layers suppress cross-talk among connection conductors and can thus suppress noise mixture into reception signals.

However, it is difficult to drastically suppress an influence of cross-talk among connection conductors or an electric influence from the outside merely by means of provision of the grounded conductive layers each being disposed between adjacent connection conductors. In particular, when the ultrasonic echo received by the ultrasound probe has a center frequency of 10 MHz or higher, its electric influence would possibly be a major cause of a decrease in the signal-to-noise ratio of reception signals.

SUMMARY OF THE INVENTION

The present invention has been made to solve the above-described problem of the prior art and has an object to provide an ultrasound probe capable of suppressing a decrease in the signal-to-noise ratio of reception signals and a method for connecting signal lines.

An ultrasound probe according to the present invention has a plurality of piezoelectric elements arranged in an array, the plurality of piezoelectric elements outputting reception signals obtained through transmission and reception of an ultrasonic beam to an ultrasound diagnostic apparatus body, the ultrasound probe comprising: a printed board on which a plurality of connection conductors are formed for connecting between a plurality of drawn-out signal lines drawn out from the plurality of piezoelectric elements and a plurality of communication cables connected to the ultrasound diagnostic apparatus body, respectively, wherein connection-conductor insulation layers are formed on the printed board so as to cover respective outer peripheries of the plurality of connection conductors, and a connection-conductor ground conductive layer is formed on the printed board so as to cover individual outer peripheries of the connection-conductor insulation layers, whereby the plurality of connection conductors are shielded from one another.

A signal line connecting method according to the present invention connects a plurality of drawn-out signal lines drawn out from a plurality of piezoelectric elements arranged in an array to an ultrasound diagnostic apparatus body through communication cables, the method comprising the steps of:

connecting the plurality of drawn-out signal lines to the plurality of communication cables through a plurality of connection conductors formed on a printed board arranged between the plurality of piezoelectric elements and the ultrasound diagnostic apparatus body; and covering outer peripheries of the plurality of connection conductors respectively with connection-conductor insulation layers formed on the printed board and covering outer peripheries of the connection-conductor insulation layers individually with a connection-conductor ground conductive layer formed on the printed board, whereby the plurality of connection-conductors that connect the plurality of drawn-out signal lines to the plurality of communication cables are shielded from one another.

DETAILED DESCRIPTION OF THE INVENTION

An embodiment of the present invention will be described below based on the appended drawings.

Figure 1:
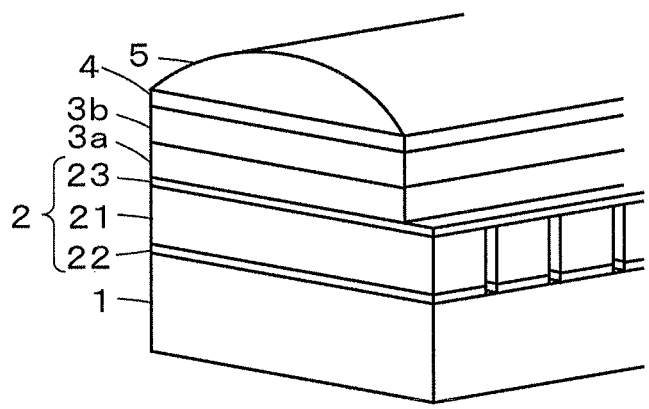
FIG. 1 is a perspective view illustrating a part of an ultrasound probe according to an embodiment of the present invention.

FIG. 1 illustrates a configuration of an ultrasound probe according to an embodiment of the present invention. A plurality of inorganic piezoelectric elements 2 are arranged at a predetermined pitch on the top surface of a backing material 1. The inorganic piezoelectric elements 2 comprise a plurality of inorganic piezoelectric bodies 21 separated from one another, and signal electrode layers 22 are respectively joined to surfaces on one side of the inorganic piezoelectric bodies 21, while a ground electrode layer 23 is joined to entire surfaces on the other side of the inorganic piezoelectric bodies 21. Thus, each of the inorganic piezoelectric elements 2 comprises a dedicated inorganic piezoelectric body 21, a dedicated signal electrode layer 22, and a part of a ground electrode layer 23.

Acoustic matching layers 3a and 3b are sequentially joined onto the inorganic piezoelectric elements 2. The acoustic matching layers 3a and 3b are not severed into a plurality of pieces and extend entirely over the inorganic piezoelectric elements 2. Further, an acoustic lens 5 is joined onto the acoustic matching layer 3b via a protection layer 4.

Figure 2:
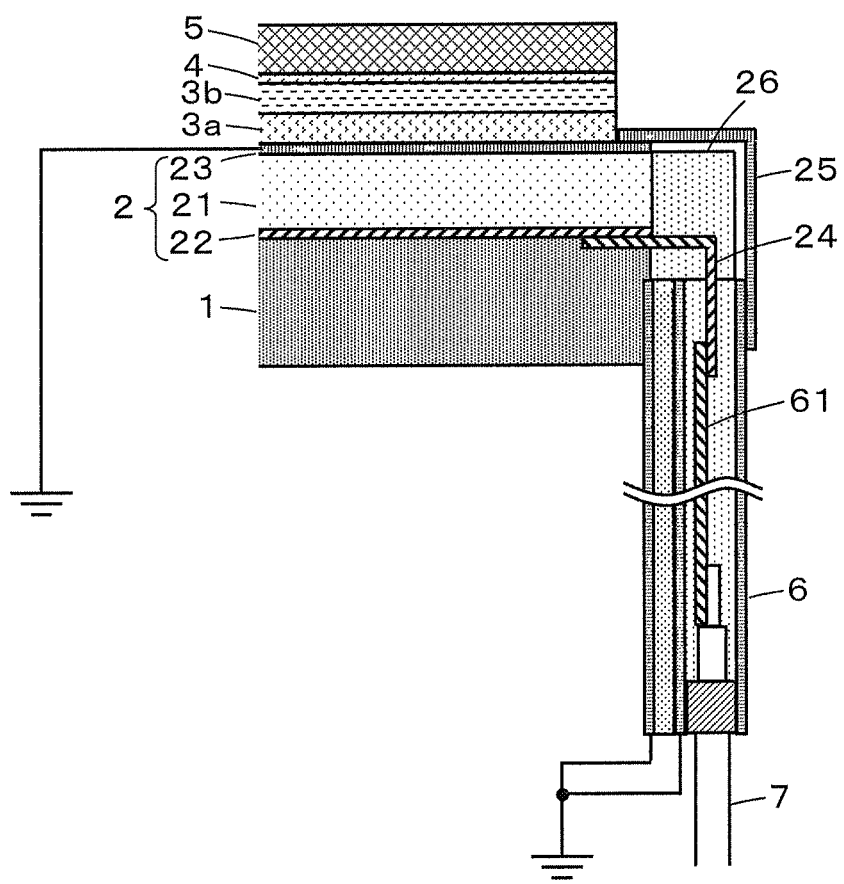
FIG. 2 is a cross section illustrating a configuration of the ultrasound probe according to the embodiment.

As illustrated in FIG. 2, the signal electrode layer 22 formed in each of the inorganic piezoelectric elements 2 extends from one end to the other end of the inorganic piezoelectric body 21, and, at the other end, the signal electrode layer 22 is connected to a drawn-out signal line 24. The drawn-out signal line 24 is connected to the signal electrode layer 22 on a one-to-one basis, is drawn out to the outside of the inorganic piezoelectric body 21 from the connection portion along the surface of the backing material 1 and is bent so as to be opposed to an end face of the backing material 1. In addition, a signal-line insulation member 26 is disposed so as to embed inside thereof a plurality of the drawn-out signal lines 24 that are drawn to the outer side of the inorganic piezoelectric bodies 21.

In the meantime, the ground electrode layer 23 formed on the inorganic piezoelectric elements 2 extends from an end to the other end of the inorganic piezoelectric body 21, which other end is connected to a signal-line ground conductive member 25. The signal-line ground conductive member 25 has a plate-like shape and is disposed so as to extend entirely over the plurality of inorganic piezoelectric elements 2. The signal-line ground conductive member 25 connected to the ground electrode layer 23 is drawn to the outer side of the inorganic piezoelectric bodies 21 from their connection portion along the surface of the inorganic piezoelectric bodies 21 and is bent so as to be opposed to end faces of the inorganic piezoelectric bodies 21. Accordingly, the signal-line ground conductive member 25 is disposed to cover the outside of the signal-line insulation member 26 in which the drawn-out signal lines 24 are embedded, whereby the signal-line ground conductive member 25 is electrically insulated from the drawn-out signal lines 24 by the signal-line insulation member 26.

A printed board 6 is arranged at an end face of the backing material 1, and the drawn-out signal lines 24 connected to the plurality of signal electrode layers 22 are respectively connected to a plurality of coaxial cables 7 connected via a plurality of connection conductors 61 formed on the printed board 6 to an ultrasound diagnostic apparatus body.

Figure 3:
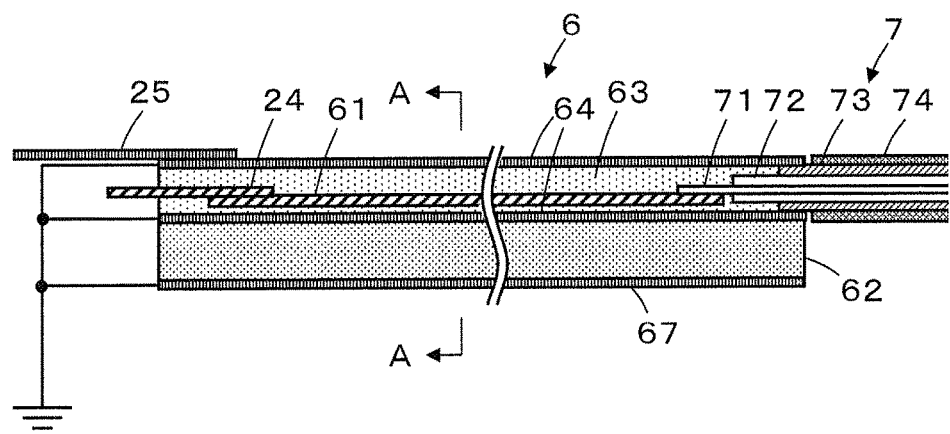
FIG. 3 is a cross section illustrating a printed board of the ultrasound probe according to the embodiment.

FIG. 3 illustrates a configuration of the printed board 6 at which the coaxial cables 7 are connected to the drawn-out signal lines 24. The printed board 6 includes a board body 62 formed of an insulating resin or the like. On a surface of the board body 62, the plurality of connection conductors 61 are formed so as to each extend from an end toward the other end of the board body 62, and a connection-conductor insulation layer 63 is formed to surround the outer periphery of each of the connection conductors 61, while a connection-conductor ground conductive layer 64 is formed to surround the outer peripheries of the respective connection-conductor insulation layers 63.

Figure 4:
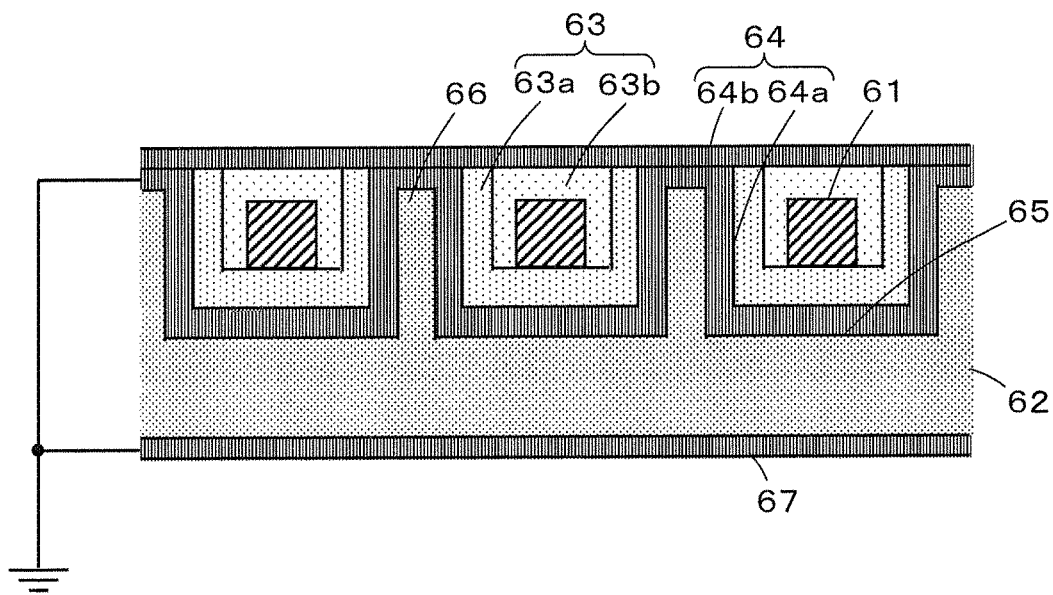
FIG. 4 is a cross section taken along a line A-A of FIG. 3.

Specifically, as illustrated in FIG. 4, the board body 62 is provided on its top surface with a plurality of guide grooves 65 that correspond to the plurality of connection conductors 61 and extend from an end to the other end of the board body 62, and each of the connection conductors 61 is disposed in each of the guide grooves 65 where the connection conductor 61 is covered by the connection-conductor ground conductive layer 64 via the connection-conductor insulation layer 63. The connection-conductor ground conductive layer 64 consists of a lower conductive layer 64a provided along the surfaces of the guide grooves 65 and an upper conductive layer 64b provided above the lower conductive layer 64a so as to entirely cover the plurality of guide grooves 65. The lower conductive layer 64a and the upper conductive layer 64b are in contact with each other on partitions 66 each separating between adjacent guide grooves 65, whereby the connection-conductor ground conductive layer 64 can thoroughly surround the outer periphery of the connection conductor 61 in each of the guide grooves 65 and can separate each of the connection conductors 61 from one another.

The connection-conductor insulation layer 63 consists of a lower insulation layer 63a disposed in contact with the lower conductive layer 64a and an upper insulation layer 63b disposed in contact with the upper conductive layer 64b. The lower insulation layer 63a and the upper insulation layer 63b throughly surround the outer periphery of the connection conductor 61, whereby the connection-conductor insulation layer 63 can electrically insulate the connection conductor 61 from the connection-conductor ground conductive layer 64.

As described above, the connection conductor 61 is disposed in each of the guide grooves 65 and has its outer periphery from one end to the other end surrounded by the connection-conductor ground conductive layer 64 via the connection-conductor insulation layer 63. In addition, as illustrated in FIG. 3, the connection conductor 61 is connected to the drawn-out signal line 24 inserted from one end into the connection-conductor insulation layer 63 and is also connected to a core wire 71 of the coaxial cable 7 inserted from the other end into the connection-conductor insulation layer 63. The coaxial cable 7 consists of a cable insulation member 72 disposed so as to cover the outer periphery of the core wire 71, a cable conductive member 73 disposed so as to cover the outer periphery of the cable insulation member 72, and a protection film 74 disposed so as to cover the cable conductive member 73.

One end of the connection-conductor ground conductive layer 64 is connected to the signal-line ground conductive member 25 connected to the ground electrode layer 23 while the other end thereof is connected to the cable conductive member 73 of the coaxial cable 7. Preferably, the guide grooves 65 are formed such that when the tip portions of the core wires 71 of the plurality of coaxial cables 7 are respectively disposed in the plurality of guide grooves 65, the core wires 71 of the plurality of coaxial cables 7 are aligned with and connected to the plurality of connection conductors 61 and the cable conductive members 73 of the plurality of coaxial cables 7 abut the plurality of connection-conductor ground conductive layers 64. Preferably, the connection conductors 61 and the connection-conductor ground conductive layer 64 have the distance therebetween, dielectric constants thereof and the like that are adjusted so as to have a characteristic impedance corresponding to that of the coaxial cables 7.

In the meantime, a rear surface of the board body 62 is joined to a board ground conductive layer 67 that is grounded. At least one of the signal-line ground conductive layer 25, the connection-conductor ground conductive layer 64 and the cable conductive member 73 is required to be grounded, and, for example, the connection-conductor ground conductive layer 64 can be connected to the board ground conductive layer 67. As described above, since the connection-conductor ground conductive layer 64 is grounded using the configuration of the printed board 6, the structure of the ultrasound probe in relation to grounding can be simplified.

Meanwhile, the inorganic piezoelectric body 21 of the inorganic piezoelectric element 2 can be formed of a lead-based oxide having a perovskite structure such as a lead-based piezoelectric ceramic typified by lead zirconate titanate ($Pb(Zr,Ti)O_3$) or a relaxor-based piezoelectric monocrystal typified by a magnesium niobate-lead titanate solid solution (PMN-PT) and a zinc niobate-lead titanate solid solution (PZN-PT). In addition, other piezoelectric elements can be also used in place of the inorganic piezoelectric element 2. Other piezoelectric elements that can be also used include, for example, an organic piezoelectric element made of a vinylidene fluoride compound such as polyvinylidene fluoride (PVDF) or a polyvinylidene fluoride trifluoroethylene copolymer (P(VDF-TrFE)).

The backing material 1 supports the plurality of inorganic piezoelectric elements 2 and absorbs the ultrasonic waves discharged backwards. The backing material 1 may be made of a rubber material such as ferrite rubber.

The acoustic matching layers 3a and 3b are provided to allow an ultrasonic beam emitted from the inorganic piezoelectric elements 2 to efficiently enter a subject and is formed of a material having an acoustic impedance between that of the inorganic piezoelectric elements 2 and that of a living body.

The protection layer 4 protects the acoustic matching layer 3b and is made of, for example, polyvinylidene fluoride (PVDF).

The acoustic lens 5 uses refraction to focus an ultrasonic beam in order to improve the resolution in the elevation direction and is formed of, for example, silicon rubber.

Next, an example of a method of producing an ultrasound probe is shown.

Figure 5A:
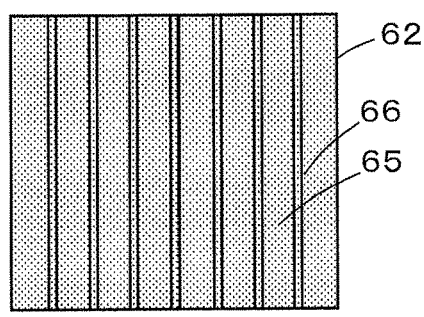
FIGS. 5A to 5F are cross sections illustrating a method of producing the ultrasound probe according to the embodiment in order of production steps.
Figure 5B:
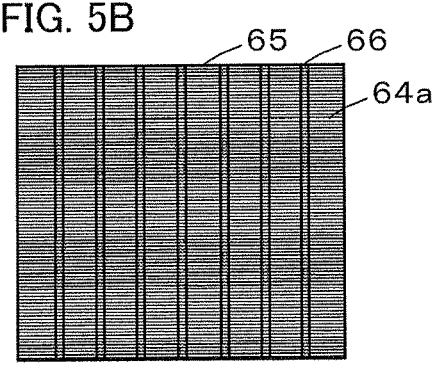

First, as illustrated in FIG. 5A, the plurality of guide grooves 65 are formed on the top surface of the board body 62 of the printed board 6 such that the guide grooves 65 extend from one end to the other end of the board body 62. At this time, the board ground conductive layer 67 that is grounded has been preliminarily formed over the entire rear surface of the board body 62. Next, as illustrated in FIG. 5B, the lower conductive layer 64a is formed over the entire top surface of the board body 62. The lower conductive layer 64a is formed along the surfaces of the guide grooves 65 that are formed on the top surface of the board body 62 to cover bottoms and sides of the connection conductors 61 that are respectively disposed in the guide grooves 65 as illustrated in FIG. 4.

Figure 5C:
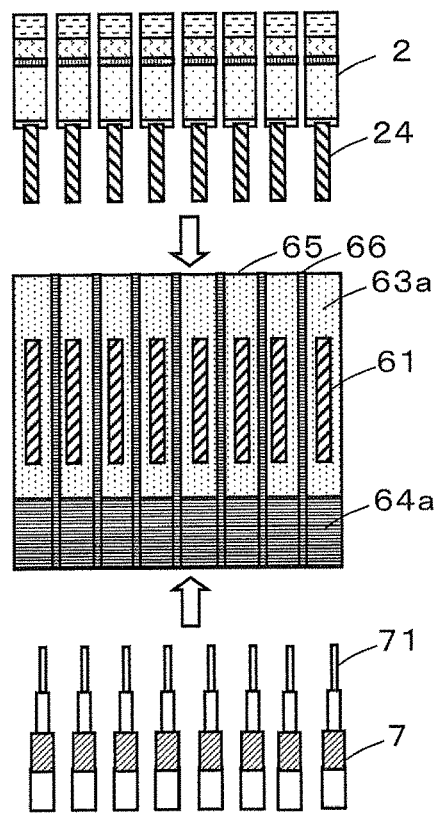

Subsequently, as illustrated in FIG. 5C, the lower insulation layers 63a each having a shape corresponding to the guide groove 65 are respectively formed in the guide grooves 65, thereby covering the surfaces of the lower conductive layer 64a. At this time, since the lower insulation layers 63a are formed so as to extend from one end to the vicinity of the other end of the board body 62 along the guide grooves 65, the lower conductive layer 64a is exposed above the partitions 66 and in the vicinity of the other end of the guide grooves 65. The lower insulation layer 63a can be constituted of a resist to protect the printed board 6, for example. The resist is coated over the entire surfaces of the lower insulation layers 63a and thereafter removed from the surfaces above the partitions 66 and in the vicinity of the other end of the guide grooves 65, whereby the lower insulation layer 63a can be formed.

Next, the plurality of connection conductors 61 are disposed on the surfaces of the lower insulation layer 63a along the corresponding guide grooves 65. In other words, the bottom and the sides of each of the connection conductors 61 disposed in one of the guide grooves 65 is covered by the lower conductive layer 64a as illustrated in FIG. 4. As the connection conductors 61 are respectively disposed along the guide grooves 65 in this manner, the connection conductors 61 can be easily arranged and guided in the predetermined direction.

The drawn-out signal lines 24 respectively connected to the inorganic piezoelectric elements 2 are then inserted into the corresponding guide grooves 65 from one end while the core wires 71 of the coaxial cables 7 are inserted into the corresponding guide grooves 65 from the other end.

Figure 5D:
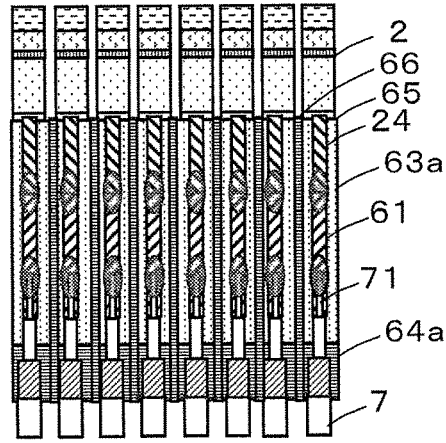

As illustrated in FIG. 5D, the drawn-out signal lines 24 inserted into the guide grooves 65 from one end and the core wires 71 of the coaxial cables 7 inserted from the other end are respectively connected to one end portions and the other end portions of the connection conductors 61 that have been preliminarily disposed in the guide grooves 65 by means of soldering or the like. As described above, the drawn-out signal lines 24 are disposed on the surfaces of the lower insulation layers 63a along the guide grooves 65. In addition, the core wires 71 and the cable insulation members 72 of the coaxial cables 7 are disposed on the surfaces of the lower insulation layers 63a while the cable conductive members 73 are also disposed so as to abut the lower conductive layer 64a exposed in the vicinity of the other end of board body 62.

Figure 5E:
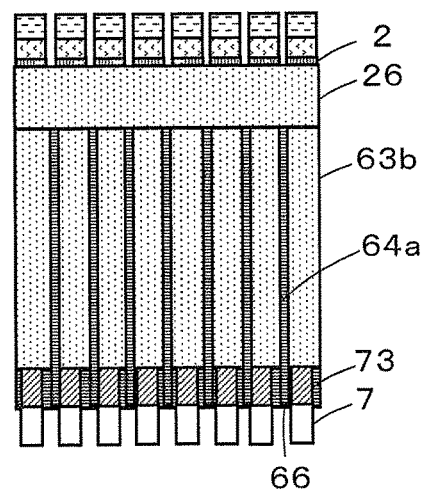

Next, as illustrated in FIG. 5E, the upper insulation layers 63b respectively fit inside the guide grooves 65 and are disposed so as to cover the top parts and the sides of the connection conductors 61 disposed in the guide grooves 65. The upper insulation layers 63b and the lower insulation layers 63a are connected to each other to constitute the connection-conductor insulation layers 63 inside the guide grooves 65 in this manner, whereby the outer peripheries of the connection conductors 61, the core wires 71 of the coaxial cables 7 and the drawn-out signal lines 24 inserted into the guide grooves 65 are thoroughly covered by insulation layers. In the meantime, the lower conductive layer 64a is exposed above the partitions 66, while the cable conductive members 73 of the coaxial cables 7 are exposed. The upper insulation layer 63b can be formed of a resin material such as epoxy resin, urethane, and acrylic resin.

Subsequently, the exposed portions of the drawn-out signal lines 24, that is, the portions between the plurality of inorganic piezoelectric elements 2 and the printed board 6 are embedded in the signal-line insulation member 26. The outer peripheries of the drawn-out signal lines 24 are then entirely covered by an insulation material.

Figure 5F:
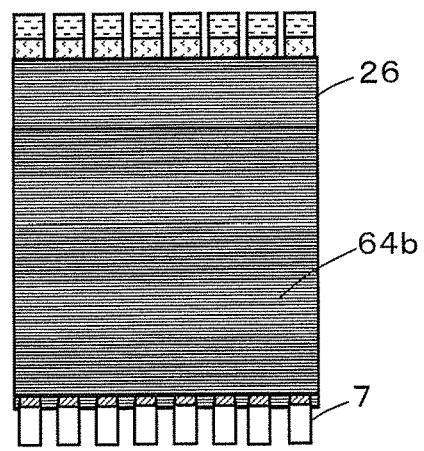

Thereafter, as illustrated in FIG. 5F, the upper conductive layer 64b is formed on the entire surface of the printed board 6 using a silver paste or the like so as to be connected to the lower conductive layer 64a above the partitions 66, whereby the connection-conductor ground conductive layer 64 is formed to thoroughly surround the outer peripheries of the connection conductors 61 via the connection-conductor insulation layers 63 in the guide grooves 65.

In addition, the signal-line ground conductive member 25 connected to the ground electrode layer 23 of the plurality of inorganic piezoelectric elements 2 is disposed so as to cover the outside of the signal-line insulation member 26, and the other end of the signal-line ground conductive member 25 is connected to the connection-conductor ground conductive layer 64. Moreover, the connection-conductor ground conductive layer 64 is connected to the board ground conductive layer 67 formed on the rear surface of the board body 62.

Accordingly, the ground electrode layer 23, the signal-line ground conductive member 25, the connection-conductor ground conductive layer 64 and the cable insulation members 72 are sequentially connected to integrally form a shielding structure, thereby shielding the drawn-out signal lines 24, the connection conductors 61 and the core wires 71 that are disposed inside the shielding structure from the outside. In addition, the connection-conductor ground conductive layer 64 is formed so as to cover the outer periphery of each of the connection conductors 65, thereby shielding each of the connection conductors 65 from one another.

Next, the operation of this embodiment will be described.

First, application of a voltage in the form of pulses or a continuous wave between the signal electrode layers 22 and the ground electrode layer 23 of the inorganic piezoelectric elements 2 causes the inorganic piezoelectric bodies 21 of the inorganic piezoelectric elements 2 to expand and contract, generating ultrasonic waves in the form of pulses or a continuous wave. The ultrasonic waves pass through the acoustic matching layers 3a and 3b, the protection layer 4, and the acoustic lens 5 to enter a subject, where the ultrasonic waves are combined to form an ultrasonic beam, which propagates inside the subject.

Subsequently, as ultrasonic echoes of the ultrasonic beam that propagated inside and reflected from the subject enter the individual organic piezoelectric elements 2 through the acoustic lens 5, the protection layer 4 and the acoustic matching layers 3a and 3b, the inorganic piezoelectric bodies 21 respond to the ultrasonic waves by expansion and contraction, generating electric signals between the signal electrode layers 22 and the ground electrode layer 23, which electric signals are outputted as reception signals from the signal electrode layers 22 to the corresponding drawn-out signal lines 24.

During this process, since the drawn-out signal lines 24 are shielded from the outside by the signal-line ground conductive layer 64 via the signal-line insulation member 26, noise mixture into the reception signals that are transmitted through the drawn-out signal lines 24 due to electric influence from the outside can be suppressed.

Next, the respective reception signals are transmitted from the drawn-out signal lines 24 to the connection conductors 61 and travel over the connection conductors 61 extending from one end to the other end of the printed board along the guide grooves 65. Since the connection conductors 61 are shielded from one another by the connection-conductor ground conductive layer 64 via the connection-conductor insulation layers 63, noise mixture into the reception signals traveling over the connection conductors 61 due to influence from electric crosstalk among reception signals can be suppressed. The reception signals having traveled over the connection conductors 61 from one end to the other end thereof without the influence of crosstalk are transmitted to the ultrasound diagnostic apparatus body from the connection conductors 61 through the core wires 71 of the coaxial cables 7.

In this way, during transmission of reception signals from the ultrasound probe to the ultrasound diagnostic apparatus body, not only the core wires 71 of the coaxial cables 7 but also the drawn-out signal lines 24 that are drawn out from the inorganic piezoelectric elements 2 of the ultrasound probe and the connection conductors 61 of the printed board 6 are shielded from the outside, and thus a decrease in the signal-to-noise ratio of the reception signals that have traveled the signal lines can be suppressed. In addition, as the plurality of connection conductors 61 formed on the printed board 6 are shielded from one another, a decrease in the signal-to-noise ratio of the reception signals can be further suppressed. In particular, when the ultrasonic echo received by the ultrasound probe has a high frequency, e.g., a center frequency of 10 MHz or higher, its reception signal is likely to be affected by an electric influence, possibly resulting in a significant decrease in the signal-to-noise ratio. However, with the ultrasound probe having the above-described shielding structure, a decrease in the signal-to-noise ratio of reception signals having a high frequency can be also suppressed.

Moreover, as the connection conductors 61 and the connection-conductor ground conductive layer 64 are constituted to have a characteristic impedance corresponding to that of the coaxial cables 7, loss of reception signals at the time when the reception signals are transmitted from the connection conductors 61 to the core wires 71 of the coaxial cables 7 can be suppressed.

Once reception signals enter the ultrasound diagnostic apparatus body via the coaxial cables 7, the ultrasound diagnostic apparatus body generates an ultrasound image based on the reception signals entered. Since a decrease in the signal-to-noise ratio of the reception signals entered in the ultrasound diagnostic apparatus body is suppressed, an ultrasound image with a high image quality can be generated. In addition, even when an ultrasound image is generated through transmission and reception of an ultrasonic beam having a high frequency, since a decrease in the signal-to-noise ratio of the reception signals is similarly suppressed, an ultrasound image with high resolution in which noise mixture is suppressed can be generated.

In the above-described embodiment, a decrease in the signal-to-ratio of reception signals is suppressed in the ultrasound probe that transmits and receives an ultrasonic beam. However, this is not the sole case, and a decrease in the signal-to-noise ratio can be suppressed in a different probe as long as the probe obtains reception signals from piezoelectric elements that receive ultrasonic waves, and an example thereof may be a probe used in photoacoustic examinations where a subject is irradiated with light to generate photoacoustic waves in the subject, and a photoacoustic image is generated based on reception signals obtained through detection of the photoacoustic waves.

What is claimed is:

1. An ultrasound probe comprising:
    a plurality of piezoelectric elements arranged in an array;
    a plurality of drawn-out signal lines drawn out from the plurality of piezoelectric elements; and
    a print board on which a plurality of connection conductors are formed for electrically connecting between a plurality of communication cables connected to an ultrasound diagnostic apparatus body and the plurality of drawn-out signal lines, respectively, whereby reception signals generated in the plurality of piezoelectric elements travel from the plurality of drawn-out signal lines to the plurality of communication cables through the plurality of connection conductors,
    wherein connection-conductor insulation layers are formed on the printed board so as to cover respective outer peripheries of the plurality of connection conductors, and a connection-conductor ground conductive layer is formed on the printed board so as to cover individual outer peripheries of the connection-conductor insulation layers, whereby the plurality of connection conductors are shielded from one another,
    a signal-line insulation member is disposed between the plurality of piezoelectric elements and the printed board so as to embed the plurality of drawn-out signal lines, and a signal-line ground conductive member having a plate shape is disposed so as to cover an outside of the signal-line insulation member, whereby the plurality of drawn-out signal lines are shielded from an outside,
    the signal-line ground conductive member is connected to ground electrodes formed in the plurality of piezoelectric elements and also to the connection-conductor ground conductive layer,
    and
    the ground electrodes, the signal-line ground conductive member and the connection-conductor ground conductive layer integrally form a shielding structure.

2. The ultrasound probe according to claim 1, wherein a plurality of guide grooves are formed on a surface of the printed board so as to extend correspondingly to the plurality of connection conductors, and the plurality of connection conductors covered by the connection-conductor insulation layers and the connection-conductor ground conductive layer are respectively disposed in the guide grooves.

3. The ultrasound probe according to claim 2, wherein tip portions of core wires of the plurality of communication cables are respectively disposed in the guide grooves formed on the printed board so that the core wires of the plurality of communication cables are aligned and connected to the plurality of connection conductors.

4. The ultrasound probe according to claim 3, wherein the plurality of communication cables include: cable insulation members formed so as to respectively cover outer peripheries of the core wires; and cable conductive members formed so as to respectively cover outer peripheries of the cable insulation members and also to connect with the connection-conductor ground conductive layer.

5. The ultrasound probe according to claim 1, wherein the plurality of communication cables connected to the ultrasound diagnostic apparatus body are constituted by coaxial cables, and
    wherein the connection conductors and the connection-conductor ground conductive layer are formed on the printed board so as to have a characteristic impedance corresponding to a characteristic impedance of the coaxial cables.

6. The ultrasound probe according to claim 1, wherein the printed board includes a board ground conductive layer on a rear surface of the printed board, and the connection-conductor ground conductive layer is connected to the board ground conductive layer.

7. The ultrasound probe according to claim 1, wherein an ultrasonic echo received by the plurality of piezoelectric elements has a center frequency of 10 MHz or higher.

8. The ultrasound probe according to claim 1, further comprising a backing material on a surface of which the plurality of piezoelectric elements are arrayed,
    wherein the plurality of piezoelectric elements includes a plurality of inorganic piezoelectric bodies, a plurality of signal electrode layers joined to one surfaces of the plurality of inorganic bodies opposing to the backing material, and a ground electrode material joined entirely to another surfaces of the plurality of inorganic piezoelectric bodies.

9. The ultrasound probe according to claim 8, wherein the printed board is arranged along an end face of the backing material.

10. The ultrasound probe according to claim 9, wherein the plurality of drawn-out signal lines are drawn out from the plurality of signal electrode layers along the surface of the backing material and are bent so as to oppose the end face of the backing material, thereby being connected to the plurality of connection conductors at an end portion of the printed board.

11. The ultrasound probe according to claim 10, wherein the plurality of connection conductors are formed on the printed board so as to extend from the end portion to another end portion opposing the end portion.

12. The ultrasound probe according to claim 11, wherein the plurality of connection conductors are connected to the plurality of communication cables at the other end portion of the printed board.

13. The ultrasound probe according to claim 8, wherein the backing material is formed of a rubber material.

14. The ultrasound probe according to claim 8, wherein the plurality of inorganic piezoelectric bodies are formed of a lead-based oxide having a perovskite structure.

15. The ultrasound probe according to claim 1, further comprising an acoustic matching layer disposed on the plurality of piezoelectric elements.

16. The ultrasound probe according to claim 15, further comprising an acoustic lens disposed on the acoustic mating layer.

17. The ultrasound probe according to claim 16, further comprising, between the acoustic matching layer and the acoustic lens, a protection layer for protecting the acoustic matching layer.

18. A method for connecting signal lines comprising the steps of:
    electrically connecting a plurality of drawn-out signal lines drawn out from a plurality of piezoelectric elements arranged in an array of an ultrasound probe to a plurality of communication cables connected to an ultrasound diagnostic apparatus body through a plurality of connection conductors formed on a printed board; and covering outer peripheries of the plurality of connection conductors respectively with connection-conductor insulation layers formed on the printed board and covering outer peripheries of connection-conductor insulation layers individually with a connection-conductor ground conductive layer formed on the printed board, whereby the plurality of connection-conductors that connect the plurality of drawn-out signal lines to the plurality of communication cables are shielded from one another, wherein reception signals generated in the plurality of piezoelectric elements travel from the plurality of drawn-out signal lines to the plurality of communication cables through the plurality of connection conductors, a signal-line insulation member is disposed between the plurality of piezoelectric elements and the printed board so as to embed the plurality of drawn-out signal lines, and a signal-line ground conductive member having a plate shape is disposed so as to cover an outside of the signal-line insulation member, whereby the plurality of drawn-out signal lines are shielded from an outside, the signal-line ground conductive member is connected to ground electrodes formed in the plurality of piezoelectric elements and also to the connection-conductor ground conductive layer, and the ground electrodes, the signal-line ground conductive member and the connection-conductor ground conductive layer integrally form a shielding structure.

* * * * *